United States Patent
Hackmann et al.

(10) Patent No.: US 7,105,674 B2
(45) Date of Patent: Sep. 12, 2006

(54) PERYLENE-DERIVATIVE BASED CRYSTALLIZATION MODIFIERS

(75) Inventors: Claus Hackmann, Kirchheim (DE); Paul Guenthert, Schifferstadt (DE); Anton Dotter, Hockenheim (DE); Peter Blaschka, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 150 days.

(21) Appl. No.: 10/839,343

(22) Filed: May 6, 2004

(65) Prior Publication Data

US 2004/0200388 A1    Oct. 14, 2004

Related U.S. Application Data

(63) Continuation of application No. 10/220,293, filed as application No. PCT/EP01/02701 on Mar. 10, 2001, now Pat. No. 6,784,301.

(30) Foreign Application Priority Data

Mar. 17, 2000 (DE) .................. 100 13 188

(51) Int. Cl.
  C07D 491/02  (2006.01)
  C09B 67/22   (2006.01)
(52) U.S. Cl. .................. 546/37; 106/493; 106/494
(58) Field of Classification Search .................. 546/37; 106/493, 494
See application file for complete search history.

(56) References Cited

U.S. PATENT DOCUMENTS

| | | | |
|---|---|---|---|
| 4,431,806 A | 2/1984 | Spietschka et al. |
| 5,248,774 A | 9/1993 | Dietz et al. |
| 5,264,034 A | 11/1993 | Dietz et al. |
| 5,271,759 A | 12/1993 | Wooden et al. |
| 5,466,907 A | 11/1995 | Vuitton |

FOREIGN PATENT DOCUMENTS

| | | |
|---|---|---|
| DE | 2 153 087 | 4/2002 |
| EP | 0 302 973 | 2/1989 |
| EP | 0 807 668 | 11/1997 |
| WO | WO 91 02034 | 2/1991 |

OTHER PUBLICATIONS

Polenov, Y. V. et al.: Structure of products of the reductive cyclization of Kubogens. Khimicheskaya Tekhnologiya, vol. 36, pp. 53-56, 1993.*

* cited by examiner

*Primary Examiner*—Charanjit S. Aulakh
(74) *Attorney, Agent, or Firm*—Oblon, Spivak, McClelland, Maier & Neustadt, P.C.

(57) ABSTRACT

Perylene derivatives of the general formula I

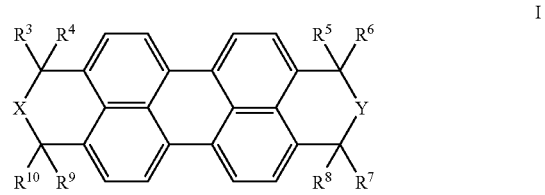

where
X and Y are independently oxygen, —$NR^1$ or —$NR^2$;
$R^1$ and $R^2$ are independently hydrogen, $C_1$–$C_{18}$-alkyl, $C_5$–$C_7$-cycloalkyl, aryl or $C_1$–$C_6$-alkoxy;
$R^3$ to $R^{10}$ are independently hydrogen, hydroxyl or aryl, although radicals conjointly attached to one carbon atom may also be =O or =$CHR^{11}$,
$R^{11}$ is hydrogen or $C_1$–$C_3$-alkyl,
with the proviso that said perylene derivative I contains from at least one to not more than three carbonyl groups per molecule.

22 Claims, No Drawings

PERYLENE-DERIVATIVE BASED CRYSTALLIZATION MODIFIERS

CONTINUING APPLICATION DATA

This application is a Continuation of application Ser. No. 10/220,293, filed on Sep. 11, 2002, now U.S. Pat. No. 6,784,301, which is a 371 of international application No. PCT/EP01/02701, filed Mar. 10, 2001.

DESCRIPTION

The present invention relates to perylene derivatives of the general formula I

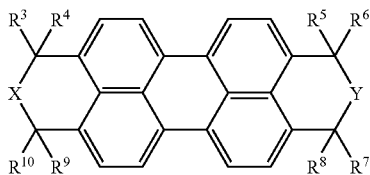

I where
X and Y are independently oxygen, —$NR^1$ or —$NR^2$;
$R^1$ and $R^2$ are independently hydrogen, $C_1$–$C_{18}$-alkyl, $C_5$–$C_7$-cycloalkyl, aryl or $C_1$–$C_6$-alkoxy;
$R^3$ to $R^{10}$ are independently hydrogen, hydroxyl or aryl, although radicals conjointly attached to one carbon atom may also be =O or =$CHR^{11}$,
$R^{11}$ is hydrogen or $C_1$–$C_3$-alkyl,
with the proviso that said perylene derivative I contains from at least one to not more than three carbonyl groups per molecule.

This invention also relates to the use of perylene derivatives I as crystallization modifiers for organic pigments and also to pigment preparations comprising the perylene derivatives I.

Perylene pigments are well known. They are notable for their high color strength and light- and weatherfastnesses and are of major importance for paint and plastics coloration. As examples of particularly interesting representatives of this class of pigment there may be mentioned N,N'-dimethylperylene-3,4,9,10-tetracarboxylic diimide (C.I. Pigment Red 179), N,N'-bis(4-phenylazophenyl)perylene-3,4,9,10-tetracarboxylic diimide (C.I. Pigment Red 178 and N,N'-bis(3,5-dimethylphenyl)-perylene-3,4,9,10-tetracarboxylic diimide (C.I. Pigment Red 149).

However, the synthesis of these pigments gives rise to crude pigments having a technically unfavorable particle shape and size, which are in need of an aftertreatment, for example as described in DE-A-21 53 087, or a salt grinding or kneading operation in order that they may be converted into a useful pigmentary form.

It is also known to add substances to influence the crystallization of the crude pigment and promote the formation of transparent pigments. For instance, in EP-A-807 668 the crude pigment is for this purpose subjected to an acid swell in the presence of anthanthrone, quinacridone and flavanthione pigments. WO-A-91/02034 describes dispersants which-are based on perylene-3,4,9,10-tetracarboxylic monoanhydride monoimides or diimides substituted by alkylene- or arylene-sulfonic acid groups on either or both imide nitrogen atoms, and which coat the pigment surface. However, these pigment preparations have different color properties as a result of the added pigment, or have only limited utility.

It is an object of the present invention to provide crystallization modifiers that will provide transparent perylene pigments having excellent application and color properties.

We have found that this object is achieved by the perylene derivatives of the formula I defined at the outset and by their use as crystallization modifiers for organic pigments.

The present invention further provides pigment preparations comprising

A) at least one organic pigment from the class of the perylene pigments and
B) at least one perylene derivative of the formula I and optionally
C) at least one rosin.

For the purposes of the invention, the perylene derivatives I shall encompass not only the "closed" structures of the formula I, but also the analogous ring-open and tautomeric structures.

Any alkyl appearing in the formula I may be straight-chain or branched. It contains up to 18 carbon atoms, although $C_1$–$C_4$-alkyl radicals, especially methyl, are preferred. Specific examples are:

methyl, ethyl, propyl, isopropyl, butyl, isobutyl, sec-butyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl and octadecyl (the above designations isooctyl, isononyl, isodecyl and isotridecyl are trivial names derived from the alcohols obtained by the oxo process).

Useful cycloalkyl radicals are cyclopentyl, cyclohexyl and cycloheptyl.

Examples of useful aryl radicals include as well as α- and β-naphthyl especially phenyl and substituted phenyl such as 4-phenylazophenyl and alkyl-substituted phenyl, eg. 3,5-dimethylphenyl, which alongside $C_1$–$C_4$-alkyl are preferred meanings of $R^1$ and $R^2$.

Any alkoxy appearing in the formula I may likewise be straight-chain or branched. Examples are methoxy, ethoxy, isobutoxy, sec-butoxy, tert-butoxy, pentoxy, isopentoxy, neopentoxy, tert-pentoxy and hexoxy.

Preference is given to perylene derivatives of the formula I where the $R^5$ and $R^6$ pair and the $R^7$ and $R^8$ pair are each =O, i.e. perylene derivatives that contain at least two carbonyl groups.

Particular preference is given to perylene derivatives of the formula I where $R^3$, $R^4$, $R^9$ and $R^{10}$ are each hydrogen or hydroxyl, although the $R^3$ and $R^4$ pair or the $R^9$ and $R^{10}$ pair can also be =O, and the $R^5$ and $R^6$ and the $R^7$ and $R^8$ pairs are each =O.

Preferably in this context only one in each pair of radicals bonded to one carbon atom is hydroxyl.

Examples of very particularly preferred perylene derivatives are:

| Perylene derivative | X | Y | $R^3, R^4$ | $R^5, R^6$ | $R^7, R^8$ | $R^9, R^{10}$ |
|---|---|---|---|---|---|---|
| Ia | O | O | OH, H | =O | =O | H, H |
| Ib | O | O | =O | =O | =O | H, H |
| Ic | O | O | H, H | =O | =O | H, H |
| Id | $NCH_3$ | $NCH_3$ | =O | =O | =O | H, H |
| Ie | $NCH_3$ | $NCH_3$ | OH, H | =O | =O | =O |
| If | O | $NCH_3$ | H, H | =O | =O | H, H |

-continued

| Perylene derivative | X | Y | R³, R⁴ | R⁵, R⁶ | R⁷, R⁸ | R⁹, R¹⁰ |
|---|---|---|---|---|---|---|
| Ig | NCH₃ | O | OH, H | =O | =O | =O |
| Ih | NC₂H₅ | O | OH, H | =O | =O | =O |
| Ik | NCH₃ | NCH₃ | H, H | =O | =O | H, H |
| Im | O | O | =CH₂ | =O | =O | =O |
| In | O | NCH₃ | =CH₂ | =O | =O | =O |

Particular emphasis is in this connection given to the perylene derivatives Ia, Ib, Ie and Ik.

The perylene derivatives I according to the invention may be prepared starting from perylene-3,4,9,10-tetracarboxylic anhydride, N-substituted or unsubstituted perylene-3,4,9,10-tetracarboxylic monoanhydride monoimides or N,N'-substituted or unsubstituted perylene-3,4,9,10-tetracarboxylic diimides as reactants.

Reduction of these reactants is an advantageous way to obtain the particularly preferred perylene derivatives of the formula I here $R^3$, $R^4$, $R^9$ and $R^{10}$ are each hydrogen or hydroxyl, although the $R^3$ and $R^4$ pair or the $R^9$ and $R^{10}$ pair can also be =O, and the $R^5$ and $R^6$ and the $R^7$ and $R^8$ pairs are each =O.

The reducing agents used for this reduction are preferably complex hydrides of the general formula II $$M^1(M^2H_mR'_n)_p \qquad \text{II}$$

where $M^1$ is a p-valent metal cation such as lithium, sodium, magnesium or aluminum;

$M^2$ is boron or aluminum subject to the proviso that $M^1 \neq M^2$;

R' is alkyl or alkoxy or, when $M^2$ is boron, cycloalkyl containing the boron atom in the ring;

m is from 1 to 4;

n is from 0 to 3 subject to the proviso that m+n=4;

p is from 1 to 3.

Examples of useful hydrides II are LiBH₄, NaBH₄, LiAlH₄, NaAlH₄, Mg(BH₄)₂, Al(BH₄)₃, LiAlH[OC(CH₃)₃]₃, NaAlH₂(C₂H₅)₂ and NaAlH₂(OC₂H₄OCH₃)₂. Of these, sodium borohydride and lithium aluminum hydride are preferred.

The reaction with the hydride II can be carried out in aqueous phase or in an organic solvent.

When sodium borohydride is used, a particularly useful reaction medium is water or a dipolar aprotic solvent that does not react with the hydride, eg. dimethyl sulfoxide, N-methylpyrrolidone or dimethylacetamide.

When lithium aluminum hydride is used, it is preferable to use an apolar aprotic solvent, for example tetrahydrofuran or diethyl ether.

Specific selection of the reaction conditions (amount of hydride II, reaction temperature and reaction time) provides trouble-free control over the reduction.

This will now be illustrated using the perylene derivatives Ia to Ic according to the invention as an example. They are advantageously preparable from perylene-3,4,9,10-tetracarboxylic dianhydride as follows:

Since in the case of these perylene derivatives I only one side of the molecule is to be reduced, it is advisable first to convert the perylene-3,4,9,10-tetracarboxylic dianhydride into the monopotassium salt, which additionally possesses higher solubility. This, after intermediate isolation or directly, can be reacted with the hydride II (eg. sodium borohydride, amount based on 1 g of perylene-3,4,9,10-tetracarboxylic dianhydride) under the conditions set out hereinafter:

0.9–1.1 g of hydride II, 10–15° C., 45–55 h→perylene derivative Ib;

1.8–2.2 g of hydride II, 50–80° C., 2–4 h→perylene derivative Ia;

3.5–4.0 g of hydride II, 90–95° C., 4–7 h→perylene derivative Ic.

After the reaction has ended, the potassium salt is converted back into the anhydride form with an acid.

It will be appreciated that the perylene-3,4,9,10-tetracarboxylic dianhydride can also be hydrogenated directly. However, owing to the lower solubility of the anhydride, higher reaction temperatures, longer reaction times and larger amounts of hydride II are needed, which is why the perylene derivatives I can frequently not be specifically prepared in this way, mixtures of various reaction products being obtained instead.

Reaction with the desired, preferably primary, amine (alkyl-, cycloalkyl-, arylamine) can then be used to convert the perylene derivatives Ib and Ic of the invention into the corresponding imides Id and If. In the case of Ia, this route customarily produces the imide Ie in a mixture with the unreduced pigment. The reaction medium used can be water or an alcohol, for example ethanol, or mixtures thereof, although water is preferred. The reaction temperatures generally range from 60 to 90° C., and the reaction can be carried out under atmospheric or superatmospheric pressure.

As further examples of inventive perylene derivatives of formula I where X is —NR¹ and Y is oxygen there may be mentioned the perylene derivatives Ig and Ih, which may be prepared analogously from the N-alkyl-substituted perylene-3,4,9,10-tetracarboxylic monoanhydride monoimide via the potassium salt using from 0.7 to 1 g of sodium borohydride per g of monoanhydride monoimide at from 55 to 60° C. over 40–55 h.

Furthermore, inventive perylene derivatives of the formula I where X and Y are each —NR¹ are obtainable by reacting the corresponding N,N'-disubstituted perylene-3,4,9,10-tetracarboxylic diimide with the hydride II by grinding at the same time. Since this reaction requires temperatures of about 100–120° C., it is advantageous to use a high boiling organic solvent, for example dimethyl sulfoxide, as reaction medium. The reaction customarily takes from 3 to 6 h. Depending on the amount of hydride used (from 0.8 to 1.1 g or from 1.7 to 2 g per g of perylimide) the perylene derivatives Ie and Ik are preparable respectively.

In principle it is also possible to combine the preparation of the perylene derivatives I with the synthesis of the perylene pigments by incipiently reducing the as-synthesized reaction mixture with a deficiency of hydride II. True, this will not provide the perylene derivatives I in a specific manner, but it does likewise provide transparent pigment preparations having excellent application properties.

Finally, reaction especially of perylene-3,4,9,10-tetracarboxylic dianhydride with organometallics may be used to provide in addition perylene derivatives I which contain a =CHR¹¹ group instead of a carbonyl oxygen atom.

Particularly useful for this purpose are organometallics of the general formula III $$(R'')_qM^3 \qquad \text{III}$$

where $M^3$ is HalMg, Li, Na or Li₂CuCN;

Hal is chlorine, bromine or iodine;

R" is alkyl, cycloalkyl, aryl or alkoxy;

q is 1 or, when $M^3$ is $Li_2CuCN$, 2.

Examples of particularly useful organometallics III are organolithiums, such as methyllithium and butyllithium, and especially the Grignard compounds R"MgHal, eg. $CH_3MgCl$, with which a $=CH_2$ group or a $—C_4H_8$ group can be introduced into the perylene derivative I.

The reaction with the organometallics III is customarily carried out in the presence of an apolar aprotic solvent, for example tetrahydrofuran.

An example of this type of reaction is the preparation of the perylene derivative In by reaction of perylene-3,4,9,10-tetra-carboxylic dianhydride with methylmagnesium chloride. A subsequent reaction with a primary amine can be used to prepare the corresponding monoimide I (eg. In).

Similarly, reaction with organometallics of the formula III'

$$R'''M^4 \qquad \qquad III'$$

where R''' is aryl and $M_4$ is lithium or sodium, can be used to introduce aryl groups into the perylene derivatives I according to the invention. A particularly useful organometallic III' is phenyllithium.

The perylene derivatives I according to the invention are very useful as crystallization modifiers for organic pigments, especially for perylene pigments.

To this end, the perylene derivatives I may be added even in the course of the pigment synthesis. Preferably, however, the perylene derivatives I are not used until the grinding of the crude pigment. Generally, the grinding is carried out in the presence of from 0.02 to 5% by weight, preferably from 0.2 to 2% by weight, of perylene derivative I, based on the resulting pigment preparation. The grinding step may usefully take the form of dry grinding, in which case it is subsequently customary to carry out a swelling step, or of a wet grind in solvents customarily used for a swelling step, especially in an aqueous medium.

To facilitate the grinding step, it is advisable to add a resin. Preference here is given to rosins, such as rosin itself and its generally known derivatives, eg. dimerized, polymerized and hydrogenated rosin and its reaction products with maleic anhydride and fumaric anhydride. It is possible to add up to 18% by weight, preferably from 8 to 15% by weight, of resin, based on the resulting pigment preparation.

It will be appreciated that further customary pigment preparation additives, such as surfactants, may be used. Suitable quantities for these additives generally range from 0 to 5% by weight.

Dry grinding can be carried out in a ball mill, in a planetary mill or in a jet mill. Wet grinding is particularly usefully carried out in a ball mill, which may be stirred, in which case it is preferably operated at from 100 to 2000 rpm. Useful grinding media include for example silicon/aluminum/zirconium oxide (SAZ) beads, glass beads, agate balls or sand grains, which may have diameters in the region of about 1 cm or in the range from 0.3 to 30 mm.

Grinding is customarily carried on until a median pigment particle size typically of about 30–100 nm is obtained. Dry grinding accordingly typically takes from 2 to 20 h, especially from 8 to 12 h.

The solvent treatment which follows the dry grinding step can be carried out in various ways.

In one variant, the millbase. (after removal of the grinding media) is swollen in a preferably concentrated mineral acid, for example in 50–100% by weight hydrochloric acid, in 50–100% by weight sulfuric acid or mixtures thereof at from 0 to 70° C. for from 2 to 20 h and then precipitated in ice-water. Preference is given to swelling in concentrated sulfuric acid (generally 75–79% by weight of sulfuric acid) at room temperature.

Another variant is the similarly conducted swelling in aqueous solutions of inorganic bases, such as sodium hydroxide, potassium hydroxide, calcium carbonate and sodium bicarbonate, or organic bases, such as methylamine. The pigment obtained is here separated from the aqueous phase by filtration.

Finally, the millbase can also be swollen in water, organic solvents or aqueous-organic mixtures. Useful organic solvents in this context are in particular water-miscible solvents, such as dimethylformamide, N-methylpyrrolidone, dimethyl sulfoxide, tetrahydrofuran and especially alkylene glycol monoalkyl ethers, in particular ethylene glycol monobutyl ether. The treatment temperatures here are generally in the range from 5 to 100° C. and the treatment times typically range from 2 to 16 h.

The similarly inventive pigment preparations include as essential pigments

A) at least one organic pigment from the class of the perylene pigments and

B) at least one perylene derivative of the formula I.

The pigment preparations preferably further include C) at least one rosin.

It will be appreciated that further customary pigment preparation additives D), for example surfactants, may be included.

The pigment preparations of the invention have the following composition in particular:

A) from 80 to 99.98% by weight, preferably from 85 to 89% by weight, of the perylene pigment, B) from 0.02 to 5% by weight, preferably from 0.2 to 2% by weight, of the perylene derivative I, C) from 0 to 18% by weight, preferably from 8 to 15% by weight, of the rosin, and D) from 0 to 5% by weight of customary additives.

Any known perylene pigments may be used. As well as perylene-3,4,9,10-tetracarboxylic dianhydride (C.I. Pigment Red 224) these include for example the unsubstituted perylene-3,4,9,10-tetracarboxylic diimide (C.I. Pigment Violet 29) and the N,N'-di($C_1$–$C_{18}$-alkyl)-, N,N'-di($C_5$–$C_7$-cycloalkyl)- and N,N'-diaryl-substituted diimides (aryl: especially phenyl and $C_1$–$C_4$-alkyl- or -alkoxy- or phenylazo-substituted phenyl) (eg.: C.I. Pigment Red 123, 149, 178, 179 and 190).

The pigment preparations of the invention are notable for their excellent application properties, especially their color properties, in particular their color strength and transparency, and their rheological properties. The pigment particles are substantially isometric with a particle size distribution typically from 50 to 100 nm.

They are very useful for coloring aqueous and nonaqueous systems. Examples of useful application media are plastics, coatings, paints, printing inks and toners.

EXAMPLES

A) Preparation of Perylene Derivatives I According to Invention

Example 1

80 g of perylene-3,4,9,10-tetracarboxylic dianhydride were dissolved in a mixture of 500 g of water and 46 g of potassium hydroxide with stirring. 50 g of 5% by weight hydrochloric acid were added to a pH of 7.3, and the precipitated potassium salt was filtered off, dried at 120° C. and then, in 800 g of ice-water, admixed with 80 g of sodium borohydride. The suspension was stirred at 10–15° C. for 48 hours and then acidified with hydrochloric acid. The product which precipitated in the process was filtered off, washed and dried at 70° C.

43 g of the perylene derivative Ib (X=Y=O, $R^3+R^4=R^5+R^6=R^7+R^8===O$, $R^9=R^{10}=H$) were obtained, which corresponds to a yield of 55%.

Analytical Data:

Red powder of melting point>300° C.;

Elemental analysis (% by weight calculated/found): C, 76.2/75.4, H: 2.6/2.8, O: 21.2/21.2, $^{13}$C-NMR (400 MHz, $D_2SO_4$): δ=179.0, 167.7, 165.3, 142.9, 140.9, 140.6, 139.2, 138.6, 135.6, 134.0, 133.2, 129.8, 129.7, 129.6, 129.5, 128.3, 127.1, 126.9, 125.0, 118.2, 117.1, 115.4, 114.2, 78.5 ppm;

IR (KBr): ν=1760 (s, C=O), 1715 (s, C=O) cm$^{-1}$.

Example 2

A mixture of 150 g of water, 30 g of the perylene derivative Ib of Example 1 and 60 g of 40% by weight aqueous methylamine solution was stirred at 85° C. for 3 h and then acidified with hydrochloric acid. The product which precipitated in the process was filtered off, washed and dried at 70° C.

24 g were obtained of the perylene derivative Id (X=Y=NCH$_3$, $R^3+R^4=R^5+R^6=R^7+R^8===O$, $R^9=R^{10}=H$), which corresponds to a yield of 75%.

Analytical Data:

Red powder of melting point>300° C.;

Elemental analysis. (% by weight calculated/found): C: 77.2/77.0, H: 3.0/3.1, O: 11.9/12.0, N: 6.9/6.9.

Example 3

Example 1 was repeated except that the intermediately isolated potassium salt of perylene-3,4,9,10-tetracarboxylic acid was reacted with 160 g of sodium borohydride at 65° C. for 3 h.

62 g were obtained of the perylene derivative Ia (X=Y=O, $R^3$=OH, $R^4$=H, $R^5+R^6=R^7+R^8===O$, $R^9=R^{10}=H$), which corresponds to a yield of 80%.

Analytical Data:

Red powder of melting point>300° C.;

Elemental analysis (% by weight calculated/found): C: 75.8/74.7, H: 3.2/3.1, O: 21.1/22.1, $^{13}$C-NMR (400 MHz, $D_2SO_4$): δ=195.5, 166.2, 164.9, 148.5, 146.4, 140.1, 138.2, 137.8, 137.1, 133.1, 133.0, 129.9, 129.6, 129.3, 128.8, 128.3, 127.7, 127.6, 127.5, 125.2, 123.6, 120.2, 116.4, 80.0 ppm;

mass (TOF-SIMS): m/z=380(M$^+$);

IR (KBr): ν=3600 (s, O—H), 1750 (s, C=O), 1710 (s, C=O), 1325 (S, C—O) cm$^{-1}$.

Example 4

Example 3 was repeated except that the potassium salt of perylene-3,4,9,10-tetracarboxylic acid was not intermediately isolated.

54 g-were obtained of the perylene derivative Ia, which corresponds to a yield of 70%.

Example 5

Example 2 was repeated except that 30 g of the perylene derivative 1a of Example 3 were used and the reaction time was 10 h.

32 g were obtained of a mixture of the perylene derivative Ie (X=Y=NCH$_3$, $R^3$=OH, $R^4$=H, $R^5+R^6=R^7+R^8=R^9+R^{10}===O$) and perylene-3,4,9,10-tetracarboxylic dianhydride.

Example 6

Example 1 was repeated except that the intermediately isolated potassium salt of perylene-3,4,9,10-tetracarboxylic acid was reacted with 300 g of sodium borohydride at 90° C. for 6 h. The filter residue of the product was additionally washed with a potassium carbonate solution.

31 g were obtained of the perylene derivative Ic (X=Y=O, $R^3=R^4$=H, $R^5+R^6=R^7+R^8===O$, $R^9=R^{10}$=H), which corresponds to a yield of 40%.

Analytical Data:

Red powder of melting point >300° C.;

$^{13}$C-NMR (400 MHz, $D_2SO_4$): δ=166.4, 146.3, 139.2, 129.7, 127.3, 126.7, 131.8, 123.7, 110.2, 70.5 ppm.

Example 7

Example 2 was repeated except that 15 g of the perylene derivative Ic of Example 6 were used.

14 g were obtained of the perylene derivative If (X=O, Y=NCH$_3$, $R^3=R^4$=H, $R^5+R^6=R^7+R^8===O$, $R^9=R^{10}$=H), which corresponds to a yield of 90%.

Analytical Data:

Red powder of melting point>300° C.;

Elemental analysis (% by weight calculated/found): C: 79.6/79.5, H: 4.0/3.9, O: 12.7/12.8, N: 3.7/3.8.

Example 8

A mixture of 2000 g of water, 10 g of N-methylperylene-3,4,9,10-tetracarboxylic monoanhydride monoimide and 4 g of potassium hydroxide was admixed with 8 g of sodium borohydride and stirred at 60° C. for 48 h. After cooling, the suspension was acidified with hydrochloric acid. The product which precipitated in the process was filtered off, washed and dried at 70° C.

7 g were obtained of the perylene derivative 1h (X=NC$_2$H$_5$, Y=O, $R^3$=OH, $R^4$=H, $R^5+R^6=R^7+R^8=R^9+R^{10}===O$), which corresponds to a yield of 70%.

Analytical Data:

Red powder of melting point>300° C.

Example 9

A mixture of 500 g of dimethyl sulfoxide, 5 g of N,N'-dimethyl-perylene-3,4,9,10-tetracarboxylic diimide and 1500 g of SAZ beads (0.4 mm in diameter) was maintained in a Dispermat at 110° C. and 2000 rpm for 4 h after addition of 4.5 g of sodium borohydride. After filtration through a coarse filter to remove the grinding media, the pH of the filtrate was adjusted with hydrochloric acid to <1.5. The product which precipitated in the process was filtered off, washed and dried at 70° C.

4.6 g were obtained of the perylene derivative Ie (X=Y=NCH$_3$, $R^3$=OH, $R^4$=H, $R^5+R^6=R^7+R^8=R^9+R^{10}===O$), which corresponds to a yield of 92%.

Analytical Data:

Red powder of melting point >300° C.;

Elemental analysis (% by weight calculated/found): C: 74.3/74.3, H: 3.8/3.8, O: 15.2/15.1, N, 6.7/6.8, $^{13}$C-NMR (400 MHz, D$_2$SO$_4$): δ=168.2, 167.4, 166.0, 164.1, 147.7, 142.4, 141.0, 137.9, 137.4, 137.3, 137.1, 132.8, 131.6, 130.8, 130.0, 129.7, 129.0, 128.9, 127.1, 126.7, 123.8, 122.9, 122.3, 121.9, .42.8, 31.5 ppm;

mass (TOF-SIMS): m/z=420(M$^+$), 403 (M$^+$—OH);

IR (KBr): ν=3371 (m, N—H), 3120 (m, Ar—H), 1693, 1656, (S, C═O) cm$^{-1}$.

Example 10

Example 9 was repeated except that 9 g of sodium borohydride were used.

4 g were obtained of the perylene derivative Ik (X═Y═NCH$_3$, R$^3$═R$^4$═H, R$^5$+R$^6$═R$^7$+R$^8$══O, R$^9$═R$^{10}$═H), which corresponds to yield of 86%.

Analytical Data:

Red powder of melting point >300° C.;

$^{13}$C-NMR (400 MHz, D$_2$SO$_4$): δ=164.1, 150.3, 140.1. 139.9, 139.0, 138.5, .132.1, 129.8. 129.1, 126.6, 126.1, 125.9, 112.0, 57.8, 45.3, 35.3 ppm;

mass (TOF-SIMS): m/z=390(M$^+$).

Example 11

A mixture of 420 g of water, 30 g of N,N'-dimethylperylene-3,4,9-10-tetracarboxylic diimide and 1 g of potassium hydroxide was admixed with 27 g of sodium borohydride and stirred at 40° C. for 20 h. After cooling, the suspension was acidified with hydrochloric acid. The product which precipitated in the process was filtered off, washed and dried at 70° C.

30 g were obtained of a mixture of perylene-3,4,9,10-tetracarboxylic dianhydride and the perylene derivative Ie of Example 9.

Example 12

A mixture of 200 g of tetrahydrofuran and 10 g of N,N'-dimethyl-perylene-3,4,9,10-tetracarboxylic diimide was admixed with 1 g of lithium aluminum hydride and stirred at 25° C. for 1 h. After cooling, the suspension was acidified with hydrochloric acid. The product which precipitated in the process was filtered off, washed and dried at 70° C.

10 g were obtained of a mixture of perylene-3,4,9,10-tetracarboxylic dianhydride and the perylene derivative Ie.

Example 13

A mixture of 500 g of water and 80 g of perylene-3,4,9,10-carboxylic dianhydride was admixed with 160 g of sodium borohydride and stirred at 70° C. for 3 h. After cooling, the suspension was acidified with hydrochloric acid. The product which precipitated in the process was filtered off, washed and dried at 70° C.

77 g were obtained of the perylene derivative Ia of Example 3, which corresponds to a yield of 99%.

Example 14

A mixture of 500 g of tetrahydrofuran and 10 g of perylene-3,4,9,10-tetracarboxylic dianhydride was admixed with 2.1 g of methylmagnesium chloride and refluxed for 10 h. The suspension was poured onto water and the mixture was acidified with hydrochloric acid. The product which precipitated in the process was filtered off, washed and dried at 70° C.

7.3 g were obtained of the perylene derivative Im (X═Y═O, R$^3$+R$^4$═══CH$_2$, R$^5$+R$^6$═R$^7$+R$^8$═R$^9$+R$^{10}$═══O), which corresponds to a yield of 70%.

Analytical Data:

Red powder of melting point>300° C.

Example 15

A mixture of 100 g of water, 10 g of the perylene derivative In of Example 14 and 60 g of 40% by weight aqueous methylamine solution was stirred at 85° C. for 3 h and then acidified with hydrochloric acid. The product which precipitated in the process was filtered off, washed and dried at 70° C.

8 g were obtained of the perylene derivative In (X═O, Y═NCH$_3$, R$^3$+R$^4$═══CH$_2$, R$^5$+R$^6$═R$^7$+R$^8$═R$^9$+R$^{10}$═══O), which corresponds to a yield of 83%.

Analytical Data:

Red powder of melting point>300° C.

B) Preparation of Pigment Preparations According to Invention

Examples 16 to 29

In Examples 16 to 28, a mixture of 25 g of crude perylene pigment P, obtained by reaction of perylene-3,4,9,10-tetracarboxylic anhydride with the corresponding primary amine in an aqueous medium under superatmospheric pressure (cf. Example 1 of DE-A-21 53 087 for C.I. Pigment Red 179),×g of the perylene derivative and y g of a thermally polymerized rosin (Dertopol®, from Granell, France) was ground in a planetary mill with 30 g of agate balls (about 1 cm in average diameter) for 10 h (Example 27: 2 h).

Example 23 utilized 25 g of the mixture obtained in Example 11 of perylene-3,4,9,10-tetracarboxylic dianhydride and perylene derivative Ie.

20 g of the millbase obtained were then swollen in 250 g of 76% by weight sulfuric acid at room temperature for 16 h. After addition to 8 l of ice-water and 30 minutes subsequent stirring, the product was filtered off, washed neutral and dried at 70° C.

In Example 29, 25 g of C.I. Pigment Red 179 mixed with perylene derivative I, rosin and 2 l of water were ground in a stirred ball mill with 400 g of SAZ beads (diameter 0.3–0.4 mm) at 1300 rpm for 2 h. After removal of the grinding media, the millbase was dried at 70° C. without additional swelling.

All cases afforded a pigment preparation which produced a transparent, very yellowish brilliant red hue in a cellulose acetate butyrate (CAB) coating system.

By comparison, a similar C.I. Pigment Red 179 which, however, had only been ground in the presence of the resin and then swollen produced a hiding, bluish dull red hue in the coating.

Further details concerning these tests are to be found in the table which follows:

TABLE

| Ex. | Perylene pigment C.I. Pigment | x g | Perylene derivative | y g of resin |
|---|---|---|---|---|
| 16 | Red 179 | 0.25 | Ib | 3.6 |
| 17 | Red 179 | 0.20 | Id | 3.6 |
| 18 | Red 179 | 0.25 | Ia | 3.6 |
| 19 | Red 179 | 0.225 | Ic | 3.6 |

TABLE-continued

| Ex. | Perylene pigment C.I. Pigment | x g | Perylene derivative | y g of resin |
|---|---|---|---|---|
| 20 | Red 179 | 0.25 | If | 3.6 |
| 21 | Red 179 | 0.12 | Ih | 3.6 |
| 22 | Red 179 | 0.25 | Ie | 3.6 |
| 23 | Red 179 | 0.25 | Mixture of Ex. 11 | 3.6 |
| 24 | Red 179 | 0.12 | Ik | 3.6 |
| 25 | Red 179 | 0.25 | Im | 3.6 |
| 26 | Red 179 | 0.15 | In | 3.6 |
| 27 | Red 178 | 0.25 | Ia | — |
| 28 | Red 149 | 0.25 | Ia | — |
| 29 | Red 179 | 0.25 | Ie | 3.6 |

We claim:

1. A perylene derivative represented by the formula I:

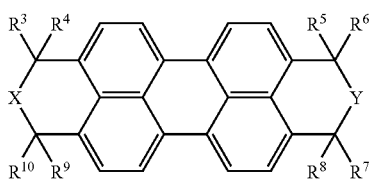

wherein
- X and Y are independently oxygen, $-NR^1$ or $-NR^2$, with the proviso that X or Y is oxygen and X and Y are not both oxygen;
- $R^1$ and $R^2$ are independently hydrogen, $C_1$–$C_{18}$-alkyl, $C_5$–$C_7$-cycloalkyl, aryl or $C_1$–$C_6$-alkoxy;
- $R^3$ to $R^{10}$ are independently hydrogen, hydroxyl or aryl, although radicals conjointly attached to one carbon atom may also represent =O or =$CHR^{11}$; and
- $R^{11}$ is hydrogen or $C_1$–$C_3$-alkyl;

with the proviso that said perylene derivative contains 1 to 3 carbonyl groups per molecule.

2. The perylene derivative of claim 1, wherein the $R^5$ and $R^6$ pair and the $R^7$ and $R^8$ pair are each =O.

3. The perylene derivative of claim 1, wherein $R^3$, $R^4$, $R^9$ and $R^{10}$ are each hydrogen or hydroxyl, although the $R^3$ and $R^4$ pair or the $R^9$ and $R^{10}$ pair may also be =O, and the $R^5$ and $R^6$ and the $R^7$ and $R^8$ pairs are each =O.

4. The perylene derivative of claim 1, wherein $R^9$ and $R^{10}$ are each hydrogen or hydroxyl, and the $R^3$ and $R^4$ pair, the $R^5$ and $R^6$ pair, and the $R^7$ and $R^8$ pairs are each =O.

5. The perylene derivative as claimed in claim 4, wherein $R^9$ $R^{10}$ are hydrogen.

6. The perylene derivative as claimed in claim 3, wherein $R^3$, $R^4$, $R^9$ and $R^{10}$ are each hydrogen or hydroxyl, or the $R^3$ and $R^4$ pair is =O, and the $R^5$ and $R^6$ and the $R^7$ and $R^8$ pairs are each =O.

7. The perylene derivative of claim 1, which contains 1 carbonyl group per molecule.

8. The perylene derivative of claim 1, which contains 2 carbonyl groups per molecule.

9. The perylene derivative of claim 1, which contains 3 carbonyl groups per molecule.

10. The perylene derivative of claim 1, wherein said aryl is α-naphthyl, β-naphthyl, phenyl, or substituted phenyl.

11. A pigment preparation comprising
A) at least one organic perylene pigment, and
B) at least one perylene derivative as claimed in claim 1.

12. The pigment preparation of claim 11, further comprising C) one or more rosins.

13. The pigment preparation of claim 12, which contains 8 to 15% by weight of C), based on the weight of the preparation.

14. The pigment preparation of claim 11, comprising:
A) from 80 to 99.98% by weight of the organic perylene pigment,
B) from 0.02 to 5% by weight of the perylene derivative,
C) from 0 to 18% by weight of a rosin, and
D) from 0 to 5% by weight of one or more additives.

15. The pigment preparation of claim 14, which comprises D), which is a surfactant.

16. The pigment preparation of claim 11, wherein the pigment is in the form of particles having a particle size distribution from 50 to 100 nm.

17. A method of preparing the pigment preparation of claim 11, comprising combining A) and B).

18. A method of modifying the crystallization of an organic pigment, comprising:
mixing the perylene derivative of claim 1 with an organic pigment; and
crystallizing the organic pigment.

19. The perylene derivative of claim 3, wherein $R^3$, $R^4$, $R^9$ and $R^{10}$ are each hydrogen or hydroxyl, or the $R^9$ and $R^{10}$ pair is =O, and the $R^5$ and $R^6$ and the $R^7$ and $R^8$ pairs are each =O.

20. The perylene derivative of claim 3, wherein X is $-NR^1$ and Y is oxygen.

21. The perylene derivative of claim 3, wherein X is $-NR^2$ and Y is oxygen.

22. The method of claim 18, wherein the organic pigment is a perylene pigment.

* * * * *